United States Patent [19]

Becker

[11] Patent Number: 5,269,724
[45] Date of Patent: Dec. 14, 1993

[54] ARRANGEMENT FOR OBTAINING GRAIN SAMPLES

[75] Inventor: Herbert Becker, Zweibruecken, Fed. Rep. of Germany

[73] Assignee: Deere & Company, Moline, Ill.

[21] Appl. No.: 901,048

[22] Filed: Jun. 19, 1992

[30] Foreign Application Priority Data

Aug. 16, 1991 [DE] Fed. Rep. of Germany ....... 4127154

[51] Int. Cl.$^5$ ..................... A01D 75/02; A01F 12/60
[52] U.S. Cl. ................................. 460/119; 460/150; 73/863.52
[58] Field of Search ............... 460/150, 23, 119, 4, 460/5, 7; 73/863.42, 863.51, 863.52, 863.53, 863.57

[56] References Cited

U.S. PATENT DOCUMENTS

| | | |
|---|---|---|
| 2,993,380 | 1/1958 | Ford . |
| 3,241,371 | 3/1966 | Horeth .................. 73/863.57 X |
| 4,393,704 | 7/1983 | Bartko ........................ 460/5 X |
| 4,574,645 | 3/1986 | Allan et al. .............. 73/863.51 |
| 4,663,978 | 5/1987 | Lenski et al. ............ 73/863.52 |

FOREIGN PATENT DOCUMENTS

| | | |
|---|---|---|
| 0180660 | 9/1988 | European Pat. Off. . |
| 7414019 | 10/1974 | Fed. Rep. of Germany . |
| 8329868 | 1/1984 | Fed. Rep. of Germany . |

Primary Examiner—Terry Lee Melius

[57] ABSTRACT

A sampling arrangement for a grain stream to extract a grain sample for analysis from the grain conveyed into a grain tank. The sampling arrangement comprises a closed crop guide that is provided with a closing arrangement that can be operated for the controlled extraction of a crop sample and transports this to a sample container of a sample extraction arrangement.

10 Claims, 2 Drawing Sheets

ARRANGEMENT FOR OBTAINING GRAIN SAMPLES

BACKGROUND OF THE INVENTION

1. Field of the Invention

The invention is directed to a sampling arrangement for obtaining a sample of grain from a flowing stream of grain. The sampling arrangement is particularly well suited for use in a grain tank of an agricultural combine. The sampling arrangement comprises a crop guide, on whose inlet the stream of grain impinges, and an outlet which directs sampled grain to a sample extraction arrangement.

2. Description of the Prior Art

Grain samples extracted from a stream of grain are used to provide samples for testing the quality of the grain contained in the grain stream at various time intervals. These arrangements are used in combines and in conveyor systems for containers of bulk materials.

DE-GM-83 29 868 discloses a sampling arrangement for a grain tank comprising a tube having an auger. The inlet of the tube is always open. The auger can be operated manually and conveys the sample constantly entering the inlet of the tube to an outlet opening.

This sampling arrangement has the disadvantage that the tube has a constant input of crop so that it cannot be determined at the outlet end from which time interval of the grain stream the particular sample was taken.

In another sampling arrangement (EP-PS-0 180 660), a chute leads from a loading conveyor entering a grain tank of a combine to a sample extraction flap, which can be tilted in one of two directions. This sampling arrangement is located in a wall of the grain tank. In a first position, the extraction flap takes in sampled grain; while in a second position, the extraction flap permits access to the sampled grain.

This sampling arrangement can be improved, since the flap is open to the interior of the grain tank and can no longer accept any additional crop beyond a certain fill level.

SUMMARY

It is an object of the present invention of providing a sampling arrangement for a stream of grain wherein the stream is sampled only when sampling is desired by the operator.

The sampling arrangement comprises a crop guide and a sample extracting arrangement. The inlet of the crop guide is arranged so that it intercepts a portion of the grain stream. The outlet of the crop guide directs the intercepted grain to the sample extracting arrangement.

By this means grain is accepted for sampling only when desired by the operator. In addition no other crop in the grain tank can intrude into the crop guide since it is provided with a closure flap. If the inlet end of the crop guide is located at the loading conveyor, it can accept grain for a sample until the fill level has reached the loading conveyor.

A sampling container may be provided, that is positioned to accept the grain sample, so that no separate container is required to accommodate the grain. Moreover this sample container permits the crop sample to be conveyed to a sampling station, for example, to determine the humidity of the crop, without the need of handling the crop which could lead to a change in the humidity.

The crop guide extends into and terminates in a housing that contains the sample container. The sample container may be arranged inside as well as outside the grain tank. The housing prevents mixing the sample with the remainder of the grain.

A simple method of determining the timing of the sample extraction from the balance of the crop is offered by the use of a closing arrangement that can be brought into a closed position or an open position at will. The opening and closing of the closing arrangement is controlled by an operator through an actuating arrangement. The closing arrangement can be configured as a closure flap, a slide or the like.

The actuating arrangement can be very simple with a spring biassing the closure flap into a closed position and a rope pull, linkage or the like being used for pulling the closure flap into an open position. The closure flap is pivotally mounted to the crop guide by a pivot shaft having an eccentric connection to the actuating arrangement for the closing arrangement.

The sampling operation as well as the extracting operation can be initiated very easily, if the operating arrangement for the actuating arrangement and the sampling container are close together, so that both operations can be performed rapidly with two hands.

The housing is provided with an outlet opening on its underside for removing excess grain sample. That is grain no longer contained in the sampling container, can fall out of the housing instead of filling it. The housing is located within the grain tank so the sample can be returned to the balance of the grain after testing through a corresponding opening in the sample extraction arrangement. If the housing is outside the collecting tank, the samples accumulating there can be removed from time to time by the use of a bag, a pail or a similar container.

Safe storage of the sample container is assured if it is retained against movement by a snap-on connection, a positive locking retention by a groove and a spring or the like.

The filling of the sample into the housing is made possible or simplified by a corresponding configuration of the sample container. This configuration is so designed that the sample container can be tilted sufficiently far into an opening, or rotated about its longitudinal axis in the opening. In the latter case the sample container can be inserted into the opening after filling and then rotated for emptying by standing it on its side.

The sample container can be easily manipulated if it is provided with a handle.

DETAILED DESCRIPTION

Figure 1:
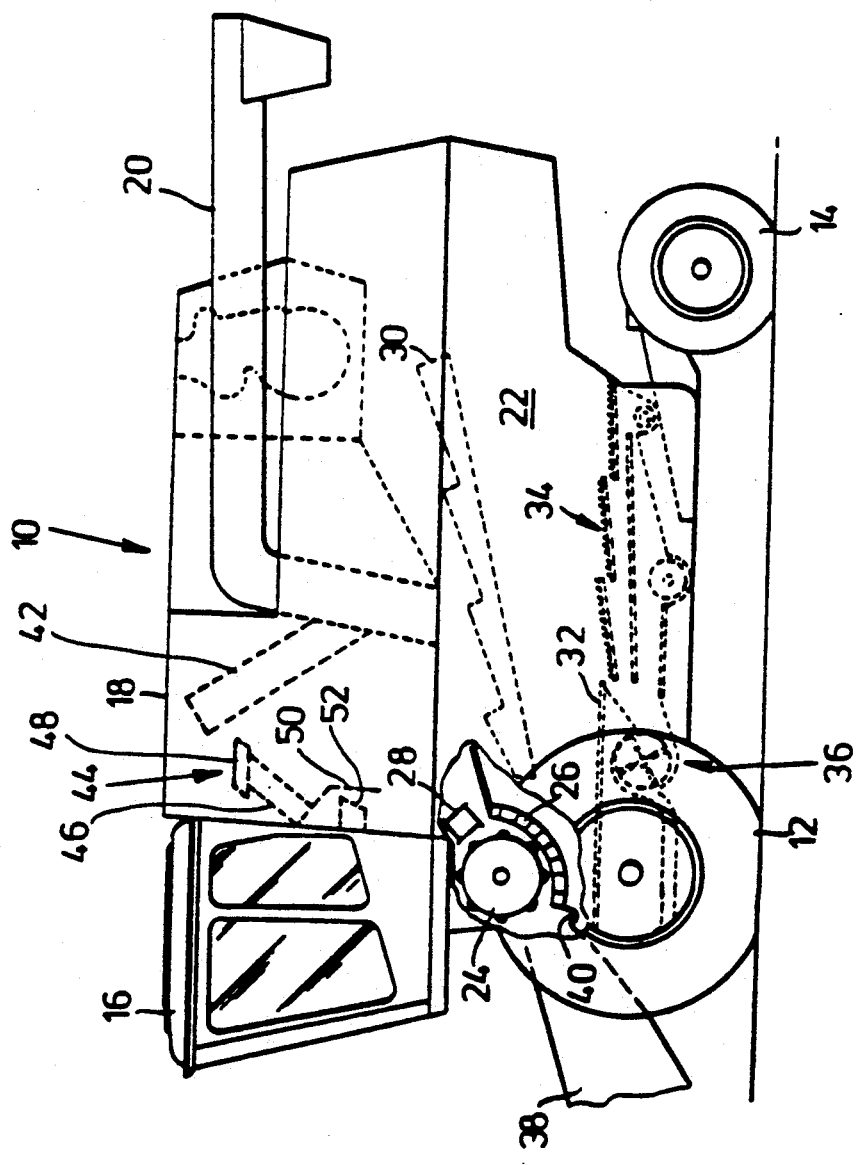
FIG. 1 is a side view of an agricultural combine with a sampling arrangement of the present invention.

A harvesting machine 10, in the form of an agricultural combine, is supported on front driven wheels 12 and rear steerable wheels 14 and is equipped with an operator's cab 16 from which it can be controlled by an operator. In place of a combine this could just as well be a stationary threshing machine, a conveyor for bulk material such as grain, corn, rice or the like. To the rear of the operator's cab 16 is a grain tank 18 for storing clean grain. The grain tank is provided with a discharge auger 20 for delivering the clean grain in the tank to a grain cart or truck. The grain tank 18 is supported on a frame 22 comprising two side sheets between which is located crop threshing, separating and cleaning assemblies.

A crop is first harvester by a harvesting platform, not shown, and then directed to feederhouse 38. The feederhouse delivers the crop to the threshing assembly comprising transverse threshing cylinder 24, concave 26 and beater 28. The threshing assembly threshes the crop, separating the grain from the other crop material. Much of the grain and chaff falls through the concave and is deposited on shaker pan 32. A stone trap 40 is located between the feederhouse and threshing assembly for trapping stones located in the crop mat delivered from the feederhouse.

The threshed crop mat is further separated by oscillating straw walkers 30. The straw walkers further remove grain trapped in the crop mat. Non-grain portions of the crop mat are expelled out the rear of the combine by the straw walkers. The grain and chaff from the straw walkers is deposited on shaker pan 32. The shaker pan 32 directs the grain and chaff to the cleaning assembly comprising cleaning shoe 34 and blower 36. Blower 36 directs and air blast up through the cleaning shoe thereby blowing the lighter weight chaff out the rear of the combine. The cleaned grain is then transported to the clean grain tank 18 by an elevator, not shown. The elevator directs the crop to loading conveyor 42. Loading conveyor 42 is an auger.

The outlet of the loading conveyor 42 is located at the intersection of the horizontal diagonals of the grain tank 18. The clean grain supplied by the loading conveyor fills the grain tank 18 from the bottom to its upper edge. The conditions, the composition and the type of crop can change during the operation of the harvesting machine, therefore grain samples are taken from the grain tank for analysis.

Samples are extracted by a sampling arrangement 44, that contains a crop guide 46 with a closing arrangement 48, a housing 50 and a sample extraction arrangement 52.

In the illustrated embodiment the sampling arrangement 44 is located inside the grain tank 18 and the sample extraction arrangement 52 is accessible from the operator's cab 16.

The crop guide 46 is formed by a tube closed along its entire length that extends within the collecting tank 18 at an angle from the housing 50 to a point immediately ahead of the outlet opening of the loading conveyor 42, so that the clean grain emerging from the outlet impinges on the inlet of the crop guide 46. The crop guide 46 is attached to the grain tank by struts, not shown.

The crop guide 46 extends through a sealed joint in an opening 54 in a cover 66 of the housing 50 and is secured there by welding. The outlet of crop guide 46 is flanged slightly to a rounded bell-mouth. The edge of the inlet is not radial to its axis, but cut at an angle to it so that it is nearly horizontal. Below the inlet the crop guide 46 is provided with a pivot shaft 56 located to one side of the longitudinal centerline of the crop guide. A short axial distance from the pivot shaft 56, a strap 58 is welded to the interior of the crop guide. The strap is provided with a bore 60.

The closing arrangement 48 is made from sheet metal in the form of a closure flap whose edges are bent downward in the shape of a hat. The flap closes off and encloses the crop guide 46 at its inlet. Two side straps 62 directed parallel to the side surface of the crop guide 46 extend beyond the pivot shaft 56 and contain bores that engage the shaft 56 to provide a pivot bearing for the closing arrangement 48. A retainer 64 is welded to the interior of the closing arrangement 48 which forms a bearing 65. The bearing 65 and the opening 60 in the strap 58 are in one line that extends parallel to the longitudinal centerline of the crop guide 46 and between the shaft 56 and the adjoining wall region of the crop guide 46.

The housing 50 comprises a cover 66 and three side walls 68 that are attached as a unit by a flange to the wall 70 of the grain tank 18. The housing 50 is open at its bottom and connected to the interior of the grain tank 18. The cover 66 is slightly inclined so that no bulk material can accumulate there when the grain tank 18 is empty. As already noted, the cover 66 is penetrated by the crop guide 46.

The sample extraction arrangement 52 comprises an opening 74 and a sample container 76.

Figure 2:
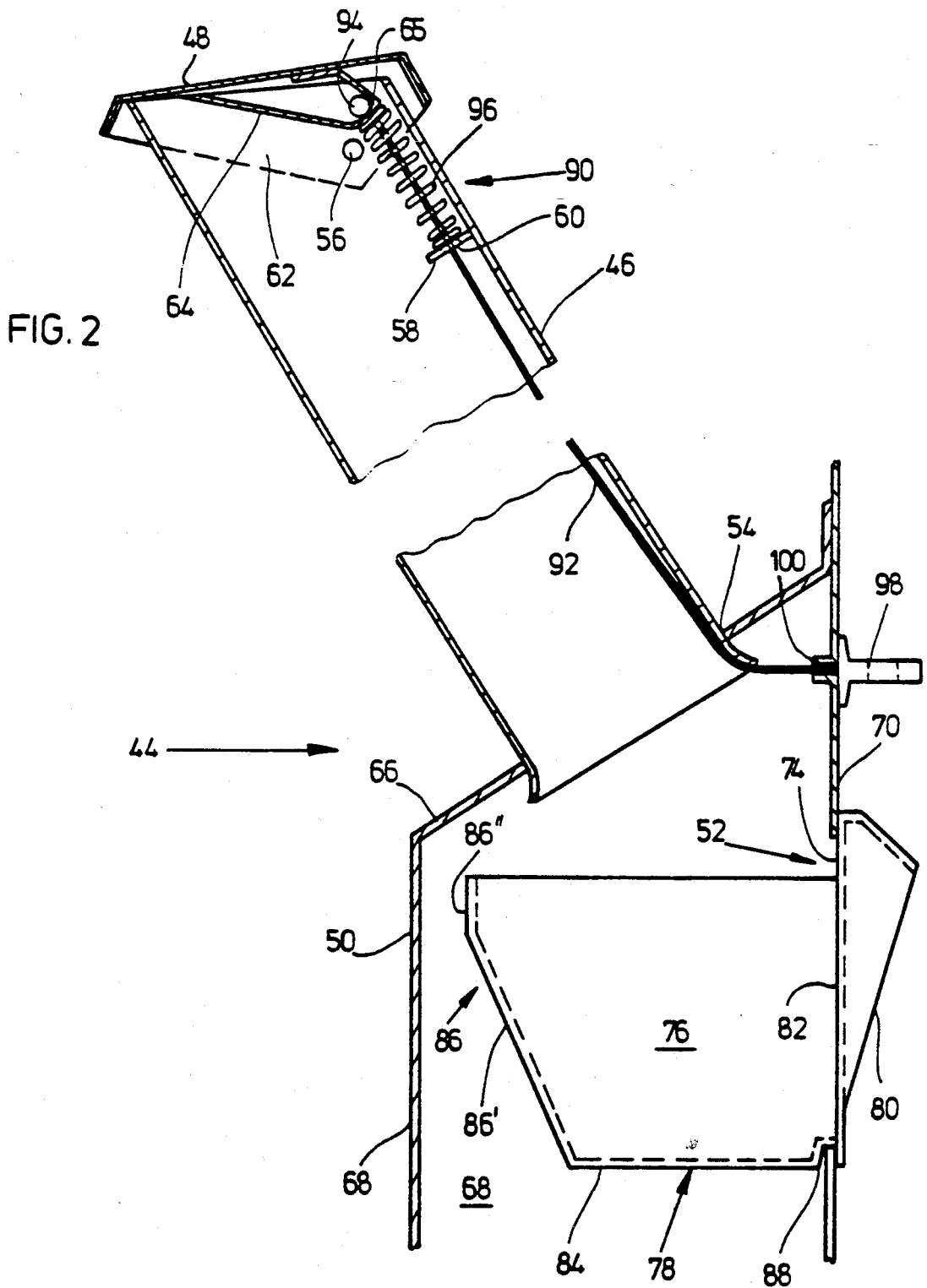
FIG. 2 is a side detailed view of the sampling arrangement.

In the embodiment illustrated in FIG. 2, the opening 74 has a square or rectangular cross section and penetrates the wall 70. In another embodiment the opening 74 may have a round cross section, however, this would require a corresponding shape for the sample container 76.

The sample container 76 contains a box 78 that is open at the top and a handle 80. In this side view, the box 78 takes on an irregular five-sided shape. The front wall 82 is aligned with the wall 70 and is at right angles to the upper edge and to a bottom 84. Opposite the front wall 82, the rear wall 86 contains an inclined, long lower section 86' and a short upper section 86" which extends at right angles to the upper edge. The box 78 is wider at the top than at the bottom. In the transition between the bottom 84 and the front wall 82 a small groove 88 is provided. The groove extends across the length of the box 78 and which is enclosed on two sides by the flanged bottom 84 and on the third side by the front wall 82. The groove 88 is so dimensioned that it can hook over the lower region of the opening 74 in the wall 70 and thereby lock the entire sample container 76 in place. While the box 78 is lower than the opening 74, the front wall 70 extends on the outside of the collecting tank 18 to all sides, in particular upward and downward beyond the opening 74 so as to cover it completely and to prevent the sample container 76 from falling into the housing 50 or into the grain tank 18. The shape of the box 78 makes it possible to set the sample container 76 with the section 86" upon the lower edge of the opening 74 in order to return the sample contained in it through the opening 74 into the housing 50.

The handle 80 is configured as a recess in the front wall 82.

Finally an actuating arrangement 90 is provided to operate the closing arrangement 48 and consists of a rope pull 92, a journal 94, a spring 96 and a pull ring 98.

The rope pull 92 extends inside the crop guide 46 from the bearing 65 through the interior of the spring 96 and the bore 60 around the flanged lower edge of the crop guide 46 through a hole 100 in the wall 70 to the pull ring 98 and is always under tension. Instead of a rope pull 92 a linkage or the like could be used.

The journal 94 is rigidly connected to the rope pull 92 and retained in the bearing 65 for which an opening, not shown, is provided in the retainer 64 through which the rope pull 92 with the journal 94 can be inserted.

The spring 96 is configured as a helical compression spring and is inserted with a certain preload between the upper side of the strap 58 and the underside of the retainer 64, and surrounds the rope pull 92. The spring 96 is designed and arranged to rotate the closing arrangement 48 about the shaft 56 in counterclockwise direction, as seen in the drawing, when the rope pull 92 is not actuated, so that it normally is in contact with and seals the upper edge of the crop guide 46.

The pull ring 98 is located outside the collecting tank 18 in contact with the wall 70 in the operator's cab 16 and can be operated from there.

On the basis of the foregoing description the sampling arrangement 44 according to the invention operates as follows. When an operator desires to take a grain sample carried by the loading conveyor 42, he pulls on the pull ring 98 and thereby swings the closing arrangement 48 in clockwise direction by means of the rope pull 92, whereupon the crop guide 46 is opened and takes in grain crop from the loading conveyor 42. This crop sample slides downward within the crop guide 46 and fills the box 78 of the sample container 76. After a short time the pull ring 98 is released, so that the closing arrangement 48, impelled by the spring 96, is closed preventing any further intrusion of crop into the crop guide 46. Following that, the sample container 76 is raised slightly until the grove 88 clears the corresponding area of the wall 70 and can be pulled towards the operator's cab. After the crop sample has been analyzed, it can be poured back through the opening 74 into the housing 50. When the grain tank 18 is unloaded the crop sample can slide downward out of the housing 50.

I claim:

1. A sampling arrangement for collecting a grain sample from a grain stream located in a grain tank, the sampling arrangement comprising:
    a downwardly sloping crop guide having an inlet that is positioned in the grain stream and an outlet;
    a closing arrangement for closing the inlet of the crop guide, the closing arrangement is normally biassed closed but can be selectively opened by an operator when selecting a grain sample;
    a housing located in the grain tank and in which the outlet of the crop guide is located; and
    a sample container is located in the housing and is in communication with the outlet of the crop guide for receiving a grain sample, when the closing arrangement is closed no grain can flow through the crop guide into the sample container located in the housing.

2. A sampling arrangement as defined by claim 1 wherein the closing arrangement comprises a closure flap that can be brought into an open or a closed position by an actuating arrangement.

3. A sampling arrangement as defined by claim 2 wherein the closure flap is biassed into its closed position by a spring.

4. A sampling arrangement as defined by claim 3 wherein the actuating arrangement that can be operated near the sample extraction arrangement.

5. A sampling arrangement as defined by claim 1 wherein the housing has an underside which is provided with an outlet opening to the grain tank.

6. A sampling arrangement as defined by claim 5 wherein the sample container is mounted to the grain tank.

7. A sampling arrangement as defined by claim 5 wherein the sample container is mounted to the housing.

8. A sampling arrangement as defined by claim 6 wherein the sample container can be pivoted relative to the grain tank.

9. A sampling arrangement as defined by claim 8 wherein the sample container is provided with a handle.

10. A sampling arrangement as defined by claim 3 wherein the closing arrangement can be pivoted about a pivot shaft and that the actuating arrangement engages a bearing arranged eccentric thereto.

* * * * *